United States Patent
Trigiante

(10) Patent No.: US 7,939,054 B2
(45) Date of Patent: May 10, 2011

(54) COMPOSITIONS FOR REMOVING HAIR

(76) Inventor: Giuseppe Trigiante, Pisa (IT)

( * ) Notice: Subject to any disclaimer, the term of this patent is extended or adjusted under 35 U.S.C. 154(b) by 50 days.

(21) Appl. No.: 11/977,968

(22) Filed: Oct. 26, 2007

(65) Prior Publication Data

US 2008/0234374 A1 Sep. 25, 2008

Related U.S. Application Data

(60) Provisional application No. 60/854,809, filed on Oct. 27, 2006.

(51) Int. Cl.
*A61Q 9/04* (2006.01)
*A61K 31/045* (2006.01)

(52) U.S. Cl. ........................ 424/70.1; 514/724

(58) Field of Classification Search ........................ None
See application file for complete search history.

(56) References Cited

U.S. PATENT DOCUMENTS

| | | | |
|---|---|---|---|
| 3,265,629 A | 8/1966 | Jensen et al. | |
| 4,962,129 A * | 10/1990 | Revici | 514/724 |
| 5,096,697 A * | 3/1992 | Adachi et al. | 424/47 |
| 5,378,455 A * | 1/1995 | Kealey et al. | 424/73 |
| 5,728,736 A | 3/1998 | Shander et al. | |
| 2005/0232981 A1* | 10/2005 | Ben-Sasson | 424/448 |

FOREIGN PATENT DOCUMENTS

| | | | |
|---|---|---|---|
| FR | 2658420 | * | 8/1991 |
| JP | 2004-196731 | | 7/2004 |
| WO | 01/80816 | | 11/2001 |

OTHER PUBLICATIONS

Erkkola et al. "Hirsutism: Definitions and Etiology" Ann. Med. 22(2):99-103 (1990).
Scott et al. "Epilation" Cutis, 46(3): 216-217 (1990).
Bowden et al. "Characterization and Chromosomal Localization of Human Hair-Specific Keratin Genes and Comparative Expression During the Hair Growth Cycle," J. Invest. Dermatol., 110(2): 158-164 (1998).
Mandt et al. "Epilation Today: Physiology of the Hair Follicle and Clinical Photo-Epilation" J. Investig. Dermatol. Symp. Proc., 10(3): 271-274 (2005).
Aldous et al. "The Effect of pH on the Toxicity of Fluoroacetic Acid" Bioohem. J. 62(4): 605-610 (1995).

* cited by examiner

*Primary Examiner* — Andrew D Kosar
*Assistant Examiner* — Lori Mattison
(74) *Attorney, Agent, or Firm* — Kenyon & Kenyon LLP

(57) ABSTRACT

The invention encompasses a composition for hair removal comprising at least one organic hair follicle penetrating agent and at least one enzyme inhibitor for the purpose of achieving permanent hair follicle inactivation, and methods for hair removal using the same.

4 Claims, 2 Drawing Sheets

Hair Follicle Structure.

Figure 1. Hair Follicle Structure.
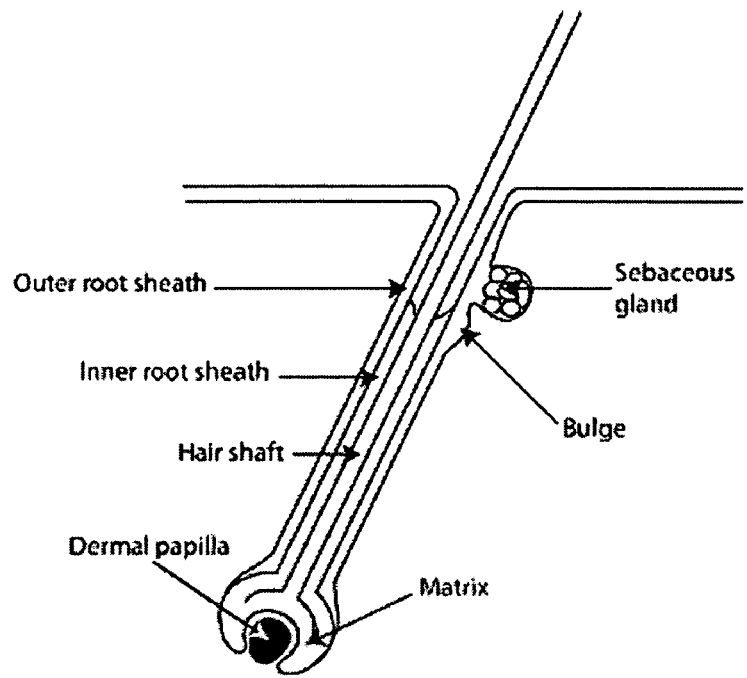
Figure 2. Hair Growth Cycle
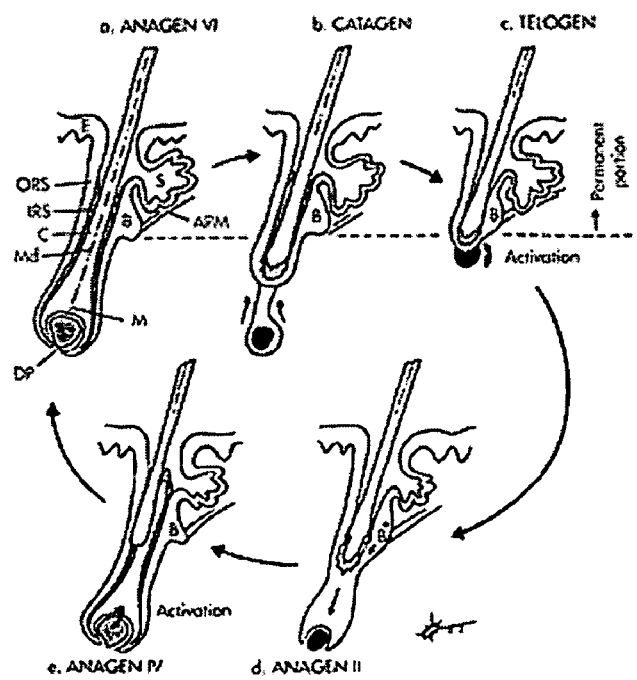

Figure 3. Empty Hair Follicle.

COMPOSITIONS FOR REMOVING HAIR

CROSS-REFERENCE TO RELATED APPLICATION

This application claims the benefit of U.S. provisional application Ser. No. 60/854,809, filed Oct. 27, 2006, hereby incorporated by reference.

FIELD OF THE INVENTION

The invention pertains to the field of permanent hair removal using a formulation endowed with the ability to reach the papilla and inactivate it, therefore resulting in weaker regrowth or ultimately permanent inactivation of the follicle.

BACKGROUND OF THE INVENTION

The overabundance of body hair (hirsutism) is caused by many factors, mainly genetic and hormonal, but it can also be caused by chemicals and medicines, such as minoxidil. Erkkola R, "Hirsutism: definitions and etiology" *Ann Med.,* 22(2):99-103 (1990). The male hormone testosterone plays a pivotal role in hormonal hirsutism as its effect on body hair is to thicken and melanize (pigment) the hair. Paradoxically, the same hormone causes an opposite effect on scalp hair, provoking androgenetic alopecia (male pattern baldness), and the two phenotypes are commonly associated. This effect is not visible before puberty and, though seen mostly in males, also affects girls. In modern society there is no biological need for body hair, except for sexual aesthetics in males. In females, though, body hair is almost always seen as unpleasant and its presence can cause distress in affected women, who generally prefer smooth bodies. Moreover, even in males the presence of excessive body hair or its localization in particular areas (back, shoulders) is unwanted and there is a growing market pressure for methods to remove them.

Hair removal has a very long history. Scott et al., "Epilation," *Cutis,* 46(3), 216-217 (1990). In ancient times all sorts of fanciful methods were used for the purpose, including tweezing and shaving with shells and pumice stones, sugaring, waxing and dissolution of the hair with caustic substances. Most of those treatments were painful and unsafe for the skin; moreover, they caused no permanent disappearance of the hair which instead grew back after varying periods. However, achieving permanent hair removal is much more difficult and only recently have permanent hair removal methods been developed.

Hair removal by chemical means is an established procedure but the effect is always temporary as no currently available chemical formulation is capable of penetrating deep into the hair follicle and reach the hair regenerative compartment, called the dermal papilla. Therefore, efficacy is limited to the hair shaft itself which is quickly regenerated by the papilla.

This is because of the hair follicle structure. FIG. 1. Every hair follicle comprises a dark, elongating column of cornified dead cells called the hair shaft. This is the visible hair and extends from the bulb to above the skin. At the base of the shaft lies a proliferating bulb which consists of a matrix of actively proliferating keratinocytes, which produce the hair shaft, surrounding a pine cone shaped organ made of mesenchimal (dermal) cells called the dermal papilla. This organ centralizes control of hair growth. It provides the matrix with the chemical signals to proliferate thus causing hair growth. At the same time it governs the hair growth cycle, which is typical of all hair. FIG. 2.

Every hair undergoes a growth phase called anagen, followed by a shedding phase called telogen, at the end of which the hair falls out and a new matrix is summoned by the dermal papilla to produce a new shaft. Bowden, et al., "Characterization and chromosomal localization of human hair-specific keratin genes and comparative expression during the hair growth cycle," *J. Invest Dermatol.,* 110(2), 158-164 (1998). This cycle continues throughout life and it is not influenced by shaving, because the external portion of the hair shaft is made of dead tissue and cannot communicate any information to the bulb. Every time a hair is plucked the traumatic event causes loss of the whole matrix and hair shaft but the dermal papilla is almost always left behind; if it weren't so tweezing would be permanent. The dermal papilla then restarts hair production just as if the hair had fallen out on its own. This is why all hair removal methods that act on the hair shaft are temporary. Only by inactivating the dermal papilla can permanent hair removal be achieved.

Current hair removal methods can be classified in two categories: methods which target the hair shaft (e.g., shaving, tweezing, waxing, sugaring) and methods which try to target the hair dermal papilla (e.g., electrolysis and laser treatment). The former are easy to implement but can only provide temporary effect. Targeting the dermal papilla is a much more complicated task because it lies deep in the dermis and it cannot be removed by mechanical means. It is very difficult to damage it without causing skin damage at the same time. Only recently have two technologies come about able to effectively target this organelle.

Hair electrolysis was first described in 1875 by a physician called Charles E. Michels. The technique involves inserting a fine metal conductor down into the hair shaft. An electric current is then applied and the hair bulb destroyed either by overheating (thermal electrolysis) or by the electrochemical local generation of caustic compounds (galvanic electrolysis). Because the hair bulb is targeted, the technique provides permanent hair removal. The main drawbacks of electrolysis are its slow rate (only one follicle can be treated per application), its painfulness, and the risk of scarring if sufficient care is not exerted. Nevertheless, electrolysis is now very popular throughout the world.

The most modern method available for permanent hair removal is performed using a laser. Mandt et al., "Epilation today: Physiology of the hair follicle and clinical photoepilation," *J. Investig Dermatol Symp Proc.,* 10(3), 271-274 (2005). This technique was first discovered accidentally in the late 1970's and has since developed into the most popular technology on the market. Laser hair removal works by applying intense pulses of laser light at a certain wavelength on the hair after it has been shaven off. The principle is that, being the hair shaft of a different color than the rest of the skin, it will absorb more of the laser radiation. This results in the overheating of the shaft itself which will transmit this heat on to the dermal papilla, damaging it.

This method is effective, although not perfect, and it does reduce the coarseness of most hair. However, it also comes with drawbacks. Because of its principle of action, it works best where there is a strong color contrast between hair and surrounding skin, i.e. ideally black hair on white skin. When this is not the case, such as for light hair or dark complexions, the method is way less effective and can cause skin damage. It does instead often cause irritation. It is also expensive because of the equipment involved and must be carried out in specialized salons. Finally, because of its unpredictable efficiency, it cannot be considered a "permanent hair removal" but a "permanent hair reduction" method and it is so advertised.

PCT publication WO 01/80816 discloses the application of a topical composition for the permanent extinction of unwanted hair-growth. However, the composition is water based, and contains an enzyme, diluter (liquid), activator (of the enzyme), and an acid. The enzyme can be selected from oxidoreductases, preferably peroxidases.

Because there are few choices as to non-invasive methods for hair removal, permanent hair removal products are needed that are easily applied to the skin and effectively reduce the regrowth of hair.

SUMMARY OF THE INVENTION

An embodiment of the invention encompasses a composition for hair removal comprising at least one organic hair follicle penetrating agent and at least one enzyme inhibitor for the purpose of achieving permanent hair follicle inactivation. The organic hair follicle penetrating agent may be a $C_1$-$C_8$ branched or linear aliphatic organic acid, $C_3$-$C_6$ ester, $C_2$-$C_{10}$ alcohol, $C_2$-$C_4$ aldehyde, or $C_3$-$C_6$ ketone. Preferably, the organic hair follicle penetrating agent is acetic acid, ethyl acetate, isopropanol, acetaldehyde, or acetone. More preferably, the hair follicle penetrating agent is isopropanol.

The enzyme inhibitor may be an inhibitor of cellular metabolism, an inhibitor of mitochondrial function, an inhibitor of protein synthesis, an inhibitor of RNA synthesis, or an inhibitor of the citric acid cycle. Preferably, the enzyme inhibitor is an inhibitor of cellular metabolism. More preferably, the inhibitor of cellular metabolism is staurosporine, carbonyl cyanide m-chlorophenylhydrazone (CCCP), valinomycin, nigercin, antimycin, oligomycin, rotenone, atractyloside, fluoroacetic acid or a fluoroacetate ester, anhydride or salt thereof. Most preferably, the inhibitor of cellular metabolism is atractyloside.

Another embodiment of the invention encompasses a methods of administering a composition for hair removal comprising removing hair by epilation (hair uprooting), applying the composition to the skin for a sufficient amount of time to induce hair removal and removing the composition from the skin. The composition may be removed from the skin no more that 10 minutes after application to the skin.

BRIEF DESCRIPTION OF THE FIGURES

FIG. 1 illustrates a hair follicle structure.
FIG. 2 illustrates the hair growth cycle.
FIG. 3 illustrates an empty hair follicle.

DETAILED DESCRIPTION OF THE INVENTION

The environment near the hair follicle is a highly hydrophobic environment which contains sebum from sebaceous glands and fatty secretions from the skin. The highly hydrophobic environment prevents any watery or water based solution from penetrating the hair follicle, because water has a high surface tension this prevents its surface from assuming the high curvature necessary to enter narrow openings such as those of a hair follicle. Besides, the hydrophobicity of the local environment does not allow water based solutions to wet the surface of the skin. The main challenge is therefore to devise a suitable penetration formula such as that presented by the invention.

The invention encompasses a different approach to permanent hair removal than water based topical compositions. Not to be limited by theory, however, it is believed that the present invention is based on the fact that, following hair epilation (plucking), the hair follicle is temporarily left vacant and therefore potentially accessible to a formulation able to penetrate it. See, FIG. 3. An appropriate composition could deliver any suitable cytotoxic agent to the bulb and dermal papilla without penetrating into and therefore damaging the surrounding skin. Hence, when the agent is a cytotoxic compound, then the dermal papilla could be inactivated and subsequent hair growth prevented. However, an obstacle to this approach is the extremely minute diameter of the hair follicle, which can be in the order of 30 micron (30 μm). Bowden et al., "Characterization and chromosomal localization of human hair-specific keratin genes and comparative expression during the hair growth cycle," *J. Invest Dermatol.*, 110(2), 158-164 (1998).

The invention encompasses topical compositions for hair removal designed to be applied to the skin after epilation (hair removal by uprooting) and capable of penetrating empty hair follicles. The composition may be in the form of a gel, paste, cream, lotion, or ointment, or on a carrier (e.g. on sponges, in dispensers or cotton applicators). The composition reaches the bulb region of the hair follicle and permanently inactivates it, thus achieving permanent hair removal. The topical composition comprises at least one organic hair follicle penetrating agent and at least one enzyme inhibitor to provoke cellular death inside the follicle lining.

The invention also encompasses methods of removing hair comprising removing hair by epilation, applying a composition for hair removal on to the skin wherein the composition comprises at least one organic hair follicle penetrating agent and at least one enzyme inhibitor to provoke cellular death inside the follicle lining, and removing the composition from the skin after a time sufficient to induce hair removal. The skin onto which the composition is applied can be the chest, back, shoulders, abdomen, arm, underarm, hands, legs, feet, toes, bikini line, face, chin, upper lip, eyebrows, or a combination thereof.

The follicle penetrating agent should penetrate the vacant hair follicles but not penetrate the skin layer and dissolve the fatty acids on the surface of the skin and wet the skin surface itself, thus allowing penetration into the hair follicle and delivery of suitable compounds to the hair bulb. Typically, the follicle penetrating agent is at least one organic acid, ester, alcohol, aldehyde, or ketone. Preferably, the organic acid is a $C_1$-$C_8$ branched or linear aliphatic saturated organic acids. More preferably, the organic acid is at least one of formic acid, acetic acid, propanoic acid, butanoic acid, pentanoic acid, hexanoic acid, heptanoic acid, or octanoic acid. Most preferably, the organic acid is acetic acid. Preferably, the ester has $C_3$-$C_6$ atoms. More preferably, the ester is at least one of methyl acetate, ethyl acetate, methyl butyrate, or butyl acetate. Most preferably, the ester is ethyl acetate. Preferably, the alcohol has $C_2$-$C_{10}$ atoms. More preferably, the alcohol is at least one of ethanol, ethylene glycol, isopropanol, butanol, pentanol, hexanol, heptanol, octanol, nonanol or decanol. Most preferably, the alcohol is isopropanol. Preferably, the aldehyde has $C_2$-$C_4$ atoms. More preferably, the aldehyde is at least one of acetaldehyde, propionaldehyde, or butyraldehyde. Most preferably, the aldehyde is acetaldehyde. Preferably, the ketone has $C_3$-$C_6$ atoms. More preferably, the ketone is at least one of acetone, butanone, pentanone, ethylisopropyl ketone, or methylisobutyl ketone. Most preferably, the ketone is acetone.

The follicle penetrating agent should be present in an amount sufficient to allow the enzyme inhibitor to reach the hair follicle. Typically, the follicle penetrating agent is present in an amount of about 50% to about 99% by weight of the composition. Preferably, the follicle penetrating agent is present in an amount of about 60% to about 95% by weight of the composition. More preferably, the follicle penetrating agent is present in an amount of about 70% to about 95% by weight of the composition and most preferably about 70 or 93% by weight of the composition.

Typically, enzyme inhibitors should inhibit the regrowth of the hair follicle. Selection of the enzyme inhibitor may be restricted by its solubility in the follicle penetrating agent and by their stability. Moreover, since the amount delivered will necessarily be minute, the enzyme inhibitor should be a compound with a suitably strong unit activity. Enzyme inhibitors include, but are not limited to, at least one inhibitor of cellular metabolism, inhibitor of mitochondrial function, inhibitor of protein synthesis, inhibitor of RNA synthesis, and inhibitor of the citric acid cycle. Typically, the inhibitor of cellular metabolism include, but are not limited to, staurosporine, carbonyl cyanide m-chlorophenylhydrazone (CCCP), valinomycin, nigercin, antimycin, oligomycin, rotenone, atractyloside, fluoroacetic acid, or fluoroacetate ester or salts thereof. Fluoroacetate ester salts include, but are not limited to, sodium fluoroacetate, potassium fluoroacetate, and the like. Fluoroacetic acid is an enzyme inhibitor, which inhibits the enzyme aconitase in the Krebs cycle in the mitochondria. Aldous et al., "The effect of pH on the toxicity of fluoroacetic acid," Biochem J. 62(4), 605-610 (1995). The inhibitors may exist as a hydrate or anhydrate form. Preferably, the inhibitor of cellular metabolism is atractyloside. Typically, the enzyme inhibitor is present in an amount of about 2% to about 50% by weight of the composition and preferably it is present in an amount of about 7% to 10% by weight.

These compositions may contain one or more stabilizers, preservatives, coloring agents, anti-inflammatory agents, water, buffering agents, thickeners, solvents, perfuming agents, and the like, and mixtures thereof.

Such stabilizers may include, but not limited to, glycol stearate or PEG-150 distearate. The stabilizer, when used, is typically present in an amount from about 0.1% to 5% by weight of the composition.

Preservatives may include, but not limited to, tetrasodium ethylene-diamine tetraacetic acid (EDTA), methylparaben, benzophenone-4, methylchloroisothiazolinone, methylisothiazolinone, and the like, and mixtures thereof. Preservatives, when used, are typically present in an amount from about 0.01% to 6% by weight of the composition, preferably about 0.05% to 4% by weight of the composition, and more preferably from about 0.1% to 2% by weight of the composition.

Coloring agents may include, but not limited to, FD&C Green No. 3, Ext. D&C Violet No. 2, FD&C Yellow No. 5, FD&C Red No. 40, and mixtures thereof. The coloring agents, when used, are typically present in an amount from about 0.001% to 0.1% by weight of the composition, and preferably from about 0.005% to 0.05% by weight of the composition.

Another embodiment of the invention encompasses methods of permanently removing hair by applying the topical composition of the invention. As used herein, the term "permanently removing hair" refers to the permanent removal of hair either in one or several treatments of the method disclosed herein. The method comprises removing hair by physical means, applying a composition for the permanent removal of hair onto the skin for a sufficient amount of time to induce permanent hair removal, and removing the composition from the skin. Physically removing the hair can be performed by epilation, such as plucking, waxing, sugaring, tweezing or other methods known in the art. Typically, the topical composition is applied on an area for a short time sufficient to induce hair removal, preferably the time sufficient to induce hair removal is about one to ten minutes, and more preferably about one to five minutes, however, the composition is not applied for more than 10 minutes, before being removed such as by being dabbed off or cleaned off with a tissue. Longer time periods, can potentially result in skin irritation and may be unnecessary, however, the skilled artisan understands that application time will depend upon the subject being treated. It is understood that the amount of the composition applied on to the skin will vary depend upon the area being treated. For example, an area covered by 100 hairs will require more solution than an area covered by 10 hairs.

Having described the invention with reference to certain preferred embodiments, other embodiments will become apparent to one skilled in the art from consideration of the specification. The invention is further defined by reference to the following example describing in detail the formation of the topical composition and methods of using the composition for the permanent removal of hair. It will be apparent to those skilled in the art that many modifications, both to materials and methods, may be practiced without departing from the scope of the invention.

EXAMPLES

Example 1

The composition was prepared by mixing the following ingredients as follows. acetic acid (93% by weight) and sodium fluoroacetate (7% by weight) were mixed to form a topical composition.

Hair (20 hairs) was removed by epilation from a 0.5 cm$^2$ area of skin. The topical composition was applied to this area of skin for one minute. Thereafter, the topical composition was removed by dabbing off. In a period of 2 months only 7 hairs had grown back and were significantly weaker than the ones originally epilated.

Example 2

The composition was prepared by mixing the following ingredients as follows. ethanol (60% by weight), water (20% by weight), acetic acid (10% by weight) and sodium fluoroacetate (10% by weight) were mixed to form a topical composition.

Hair (20 hairs) was removed by epilation from a 10 cm$^2$ area of skin. The topical composition was applied to this area of skin for 5 minutes. Thereafter, the topical composition was removed by dabbing off. In a period of 4 months about 50% of the hair had grown back and were significantly weaker than the ones originally epilated. In a control area where the formulation had not been applied all hair were found to have grown back in the same time period.

What is claimed is:

1. A topical composition for hair removal comprising at least one organic hair follicle penetrating agent and at least one enzyme inhibitor, wherein the organic hair follicle penetrating agent is heptanol and the enzyme inhibitor is atractyloside.

2. The composition according to claim 1, wherein the follicle penetrating agent is present in an amount of about 50% to about 99% by weight of the composition.

3. The composition according to claim 1, wherein the enzyme inhibitor is present in an amount of about 2% to about 50% by weight of the composition.

4. A method for hair removal comprising:
removing hair by epilation,
applying the composition of claim 1 onto an application area for a time sufficient to induce hair removal; and
removing the composition from the application area.

* * * * *